United States Patent [19]

Kurath

[11] 4,338,309

[45] Jul. 6, 1982

[54] 4',5'-DIHYDRO-ANTIBIOTIC AX-127B-1; 2'-N-DES-β-LYSYL-4',5'-DIHYDRO-ANTIBIOTIC AX-127B-1; AND 4-N-DERIVATIVES THEREOF

[75] Inventor: Paul Kurath, Waukegan, Ill.

[73] Assignee: Abbott Laboratories, North Chicago, Ill.

[21] Appl. No.: 205,815

[22] Filed: Nov. 10, 1980

[51] Int. Cl.$^3$ .................. A61K 31/71; C07H 15/22
[52] U.S. Cl. ................................. 424/180; 424/181; 435/80; 536/16.8
[58] Field of Search ............. 424/180, 181; 536/17 B, 536/17 R

[56] References Cited

U.S. PATENT DOCUMENTS

| | | | |
|---|---|---|---|
| 4,091,032 | 5/1978 | Tadanier et al. | 536/17 R |
| 4,145,253 | 3/1979 | Iida et al. | 536/17 R |
| 4,187,299 | 2/1980 | Post | 536/17 R |
| 4,241,182 | 12/1980 | Takasawa et al. | 536/17 R |
| 4,283,529 | 11/1981 | Rosenbrook, Jr. | 424/180 |

OTHER PUBLICATIONS

Rinehart, Jr. et al., "Aminocyclitol Antibiotics", 1980, pp. 309–320.
Tadanier et al., "Carbohydrate Research", vol. 79, pp. 91–102, vol. 85, pp. 61–71, 1980.

*Primary Examiner*—Johnnie R. Brown
*Attorney, Agent, or Firm*—Joyce R. Niblack; Gildo E. Fato; Dennis K. Shelton

[57] ABSTRACT

4',5'-Dihydro-antibiotic AX-127B-1, 2'-N-des-β-lysyl-4',5'-dihydro-antibiotic AX-127B-1, the 4-N-acyl and alkyl derivatives thereof and their pharmaceutically acceptable salts. The compounds are useful as antibiotics and as intermediates for preparing the corresponding 3-O-demethyl derivatives of antibiotic AX-127B-1.

68 Claims, No Drawings

4',5'-DIHYDRO-ANTIBIOTIC AX-127B-1; 2'-N-DES-β-LYSYL-4',5'-DIHYDRO-ANTIBIOTIC AX-127B-1; AND 4-N-DERIVATIVES THEREOF

BACKGROUND OF THE INVENTION

Antibiotic AX-127B-1 is a relatively new aminoglycoside antibiotic (See allowed claims of commonly assigned, copending U.S. Ser. No. 008,378, filed Feb. 1, 1979).

Chemical modification of other aminoglycoside antibiotics, as with other classes of antibiotics, has been found to improve the activity, either intrinsic or against resistant strains of organisms, or to reduce the toxicity of the parent antibiotics. And, because of the development of aminoglycosideresistant strains and inactivation of the parent antibiotics by R-mediated factors which can develop, the search continues for new entities which are either superior to known aminoglycosides or which provide an alternative therapy when resistant organisms develop.

One such modification, 2'-N-des-β-lysyl antibiotic AX-127B-1 and the 4-N-derivatives thereof, are disclosed in U.S. Ser. No. 205,813, filed of even date herewith. The present invention provides further modifications of antibiotic AX-127B-1.

SUMMARY OF THE DISCLOSURE

The present invention provides 4',5'dihydro-antibiotic AX-127B-1, 2'-N-des-β-lysyl-4',5'-dihydro-antibiotic AX-127B-1, the 4-N-acyl and alkyl derivatives thereof and their pharmaceutically acceptable salts. The compounds are useful as antibiotics and as intermediates for preparing the corresponding 3-O-demethylderivatives of antibiotic AX-127B-1.

DETAILED DESCRIPTION OF PREFERRED EMBODIMENTS

Antibiotic AX-127B-1 is represented by the formula:

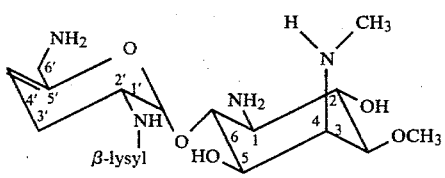

2'-N-des-β-lysyl antibiotic AX-127B-1 and its 4-N-acyl and alkyl derivatives are represented by the formula:

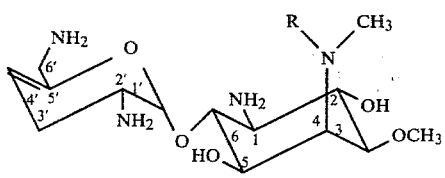

The 4',5'-dihydro derivatives antibiotic AX-127B-1 and 2'-N-des-β-lysyl-antibiotic AX-127B-1 and the 4-N-acyl and the alkyl derivatives thereof of the present invention are represented by the formula:

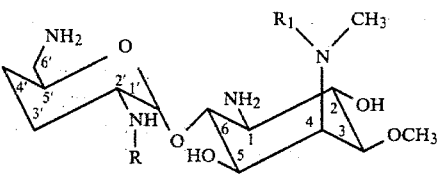

wherein: R is selected from the group consisting of hydrogen or β-lysyl; $R_1$ is selected from the group consisting of hydrogen, acyl, aminoacyl, diaminoacyl, N-loweralkylaminoacyl, N,N-diloweralkylaminoacyl, hydroxy-substituted aminoacyl, loweralkyl, aminoloweralkyl, diaminoloweralkyl, hydroxyloweralkyl, N-loweralkylaminoloweralkyl, N,N-diloweralkylaminoloweralkyl, N-loweralkylaminohydroxyloweralkyl, and N,N-diloweralkylaminohydroxyloweralkyl, and the pharmaceutically acceptable salts thereof.

The term "acyl", as used herein, refers to acyl radicals of loweralkylcarboxylic acids represented by the formula -COR wherein R is loweralkyl, i.e. acetyl, propionyl, butyryl, valeryl, etc.

The terms aminoacyl, hydroxy-substituted aminoacyl, etc. include, but are not limited to naturally occurring amino acids such as glycyl, valyl, alanyl, sarcosyl, lysyl, leucyl, prolyl, seryl, and the like as well as groups such as 2-hydroxy-4-aminobutyryl and the like. The amino acid residues, with the exception of glycyl, beta-alanyl and other non-asymmetric amino acids residues, can be either in the D or L configuration or mixture thereof.

The term "loweralkyl", as used herein, refers to straight or branched chain alkyl radicals containing from 1 to 6 carbon atoms, inclusive, and includes, but is not limited to methyl, ethyl, n-propyl, iso-propyl, n-butyl, iso-butyl, tert-butyl, n-pentyl, 1-methylbutyl, 2,2-dimethylpropyl, n-hexyl, 2-methylpentyl and the like.

The substituted amino groups are well known in the art and include, for example, beta-aminoethyl, N-methylaminoethyl, N,N-dimethylaminopropyl, hydroxyethyl, 2-hydroxy-4-aminobutyl, and the like.

The term "pharmaceutically acceptable salts" refer to the non-toxic acid addition salts which can be prepared either in situ during the final isolation and purification or by separately reacting the free base with a suitable organic or inorganic acid by methods well known in the art. Representative salts include the mono or per salts such as the hydrochloride, hydrobromide, sulfate, bisulfate, tetrahydrochloride, acetate, oxalate, valerate, oleate, palmitate, stearate, laurate, borate benzoate, lactate, phosphate, tosylate, citrate, maleate, fumarate, succinate, tartate, napsylate, and the like.

The compounds of this invention are useful as an antibacterial agent against susceptible strains of gram negative and gram positive bacilli such as *Staphylococcus aureus, Escherichia coli, Psuedomonas aeruginosa, Bacillus subtilis, Proteus vulgaris, Shigella sonnei, Salmonella typhi* and *Klebsiella penumonia*. The presently preferred antibiotics of this invention are 4',5'-dihydroantibiotic AX-127B-1 and 2'-N-des-β-lysyl-4'5'-dihydro-antibiotic AX-127b-1 and their pharmaceutically acceptable salts.

The term "susceptible strains" refers to strains of bacilli or organisms which have been demonstrated to be sensitive to a particular antibiotic in a standard in vitro sensitivity test and thus in vitro activity has been established for a particular organism. It is good medical practice to select the antibiotic of choice by the use of such in vitro tests.

The preferred antibiotics of this invention are administered parenterally, i.e. intravenously, intramuscularly, intraperitoneally, or subcutaneously for systemic effect in daily dosages of from about 5 to 50 mg/kg of body weight daily, and most preferably from about 7 to 10 mg/kg of body weight daily, based on lean body weight. It is further preferred to administer the antibiotics in divided dosages, i.e. to 3 to 4 times daily. Oral dosages to sterilize the intestinal tract are also contemplated by the present invention.

The 4-N-acyl and alkyl derivatives, in addition to their antibacterial activity are useful, as is the parent compound of this invention, as intermediates for preparing O-demethyl derivatives thereof, as disclosed in commonly assigned, copening U.S. Ser. No. 126,732, filed Mar. 3, 1980, now U.S. Pat. No. 4,283,529.

The compounds of this invention can be O-demethylated to provide the above O-demethyl derivatives thereof by dissolving the compound to be O-demethylated in, for example, methylene chloride, cooling the reaction mixture to a temperature of from about −72° C. to about 30° C., preferably 0° C., and treating the reaction mixture with from about 10 to about 100 equivalents of a boron trihalide, preferably boron tribromide, with stirring, for about 10 to about 60 minutes, at a temperature of of between −72° C. to 100° C., preferably from about 4° C. to about 38° C. Solvent and residual boron trihalide are removed in vacuo, the reaction mixture is treated with an appropriate solvent such as methanol to remove residual solvent and boron trihalide and evaporated to a residue to provide the desired derivative.

4-N-acyl derivatives of 2′-N-des-β-lysyl-4′,5′-dihydro antibiotic AX127B-1 are prepared by reacting the parent compound with o-nitro(benzyloxycarbonyloxy)succinimide to afford the 1,2′,6′-tri-N-o-nitrobenzyloxycarbonyl intermediate according to the procedure set forth in U.S. Pat. No. 4,091,032. The product formed in the above reaction is isolated by column chromatography and 4-N-acylated following the procedure of U.S. Pat. No. 4,091,032 or by treatment with, for example, azide coupling by reaction with a suitably N-protected (e.g. o-nitrobenzyloxycarbonyl)amino acid azide. The per-N-protected intermediates are conveniently reduced to the corresponding 4-N-alkyl derivatives with diborane. After isolation by column chromatography, the N-protecting groups of both the 4-N-acyl and alkyl derivatives are conveniently removed by the method of U.S. Pat. No. 4,091,032, or by photolysis, by for example, using an ultra violet light and an inert solvent such as ethanol and isolating the products, as the free base or as a salt. 4-N-Acyl derivatives of 4′,5′-dihydro antibiotic AX-127B-1 are prepared by the procedure disclosed in U.S. Pat. No. 4,091,082.

The following examples further illustrate the present invention.

EXAMPLE 1

Fermentation of Antibiotic AX-127B-1

Culture AB-127B-46 was maintained on ATCC medium #172 agar slants consisting of 1% glucose, 2% soluble starch, 0.5% Difco yeast extract, 0.5% N-Z amine type A (Sheffield Chemical Co.), 0.1% CaCO₃, 1.5% agar, and distilled water QS to 1 liter.

First passage inoculum seed tubes (25×150 mm) containing 10 ml. of sterile S-3 seed medium (Table 5) and closed with Bellco stainless steel caps were inoculated with a sterile loop from ATCC medium #172 agar slant cultures of AB-127B-46. Seed tubes were incubated on a rotary shaker (250 r.p.m.) at 30° C. for 96 hours. At that time 5% vegetative inoculum from the first passage seed tube was transferred aseptically to 500 ml. Erlenmeyer flasks containing 100 ml. of sterile S-3 seed medium and closed with cotton plugs. Inoculated second passage seed flasks were then incubated on a rotary shaker (250 r.p.m.) at 30° C. for 72 hours. Antibiotic production fermentation flasks (500 ml. Erlenmeyer) containing 100 ml. of sterile AFlb medium (Table 1) and closed with cotton plugs were inoculated with 5% vegetable inoculum from the second passage seed flasks.

The inoculated AFlb antibiotic production medium flasks were then incubated on a rotary shaker (250 r.p.m.) at 30° C. for 5 to 7 days and then harvested.

The harvested whole culture fermentation beer from a series of flasks was pooled (30 liters), adjusted to pH 2 with sulfuric acid and clarified by centrifugation or by filtration through celite. The clarified fermentation liquor was then poured into a 6.5 cm. diameter glass column containing 0.7 liters of AMBERLITE IRC 84 cation exchange resin (ammonia form). The active antibiotic was adsorbed on the resin and the effluent beer was discarded. The resin column was washed thoroughly with water. Antibiotic activity was then eluted with 1 N aqueous ammonia. Active fractions were determined by dipping paper discs in eluate fractions and testing for activity on agar plates seeded with *Staphylococcus aureus* ATCC 6538P. Active fractions were combined and concentrated to remove excess ammonia and were then neutralized to pH 6.5 with sulfuric acid. The concentrate was then passed through a glass column containing REXYN 102 (NH₄+) 2 cm. diameter×6 cm. in height or 18 ml. of resin. The column was washed with water and then eluted by stepwise gradient with aqueous ammonia starting with 0.05 N and increasing to 1 N ammonia.

Active fractions were again located by the paper disc method and further examined by both paper chromatography and thin-layer chromatography as previously described. Active fractions containing the antibiotic described in this invention were combined, concentrated to remove excess ammonia, neutralized to pH 6.5 with sulfuric acid and reduced to dryness under vacuum. The sulfate salt of the antibiotic was dissolved in distilled water and converted to free base by passing through a small glass column containing DOWEX 1-X2 (OH−).

TABLE 1

| Ingredient | gm/liter |
| --- | --- |
| S-3 Seed Medium | |
| Staclipse J soluble starch (Staley) | 24 |
| glucose monohydrate | 1 |
| yeast extract (Difco) | 5 |
| tryptone (Difco) | 5 |
| beef extract (Wilson) | 3 |
| CaCO₃ | 4 |
| tap water QS to 1.0 liter | |
| sterilization: 30 min., 121° C. at 15–16 lb. pressure | |
| AFlb Fermentation Medium | |
| glucose monohydrate | 10 |
| peptone (Difco) | 5 |
| yeast extract (Difco) | 5 |
| CaCO₃ | 1 |
| pH 7.3 | |

| TABLE 1-continued |  |
| --- | --- |
| Ingredient | gm/liter |
| tap water QS to 1.0 liter |  |
| sterilization: 30 min., 121° C. at 15–16 lb. pressure |  |

EXAMPLE 2

Isolation of Antibiotic AX-127B-1

Culture AB-127B-46 was inoculated into first passage 500 ml. Erlenmeyer seed flasks containing 100 ml. of sterile S-3 seed medium and closed with cotton plugs. Inoculated flasks were incubated on a rotary shaker (250 r.p.m.) at 30° C. for 96 hours. At that time, 5% vegetative inoculum was transferred into similar 500 ml. Erlenmeyer flasks containing 100 ml. of sterile S-3 seed medium. Inoculated second passage seed flasks were incubated on a rotary shaker at 30° C. for 72 hours. Second passage seed flasks were used to inoculate a series of 30 liter stainless steel fermentors at a level of 5% inoculum. Fermentation conditions for 30 liter fermentors were as follows:

| Fermentation Medium: | AF1b (see Table 5) |
| --- | --- |
| Fermentor Volume: | 12 liters |
| Sterilization Time: | 1 hr., 121° C., 15–16 lb pressure |
| Antifoam: | .01% P-2000 polyethylene glycol (Dow Chemical Co.) |
| Incubation Temp.: | 30° C. |
| Agitation: | 250 r.p.m. |
| Impeller Blade Angle: | 45° |
| Air Rate: | 1 volume/volume/min. |

Fermentors were incubated for 5 days and then harvested. The desired antibiotic described in this invention was isolated and purified as described in the Example 1.

EXAMPLE 3

2'-N-Des-β-lysyl antibiotic AX-127B-1

A total of 4.66 g of the sulfate salt of antibiotic AX-127B-1 (prepared according to the method of U.S. Ser. No. 008,378, filed Feb. 1, 1979 and as described above in Examples 1 and 2) are converted to the free base by treatment with AG 2×8 resin (OH−) form, Biorad Laboratories, to afford 2.71 g of the free base after lyophilization. Raman spectrum $\nu_{max}$ 1690 cm$^{-1}$. The latter is refluxed gently in 25 ml of hydrazine hydrate for 22 hours. Evaporation of the hydrazine left a residue of 2.755 g of crude product. The crude product is chromatographed on 140 g of silica gel in the lower phase of methanol-methylene chlorideammonium hydroxide[1:1:1(v/v/v)]. Ten ml fractions are collected and a total of 1.325 g of product are obtained.

EXAMPLE 4

(5'S)4',5'-Dihydro-antibiotic AX-127B-1

A total of 5.119 g of the sulfate salt of antibiotic AX-127B-1 are converted to the free base as described in Example 3 and the aqueous eluates are lypholized to afford a total of 3.077 g of the free base. The free base is dissolved in 150 ml of methanol and hydrogenated over 6 g of 20% Pd/C(50% wet) for a total of 74 hours. Evaporation of the solvent leaves 3.044 g of residue which was chromatographed on 210 g of Woelm silica gel in the lower phase of methanol-methylene chloride-ammonium hydroxide [1:1:1(v/v/v)]. Twenty ml fractions are collected and a total of 0.31 g of product obtained.

EXAMPLE 5

2'-N-Des-β-lysyl-(5'S)4',5'-dihydro-antibiotic AX-127B-1

2'-N-Des-β-lysyl-(5'S)4',5'-dihydro-antiobiotic AX-127B-1 is prepared by the method of Example 4 from 2'-N-des-β-lysyl-antibiotic AX-127B-1.

EXAMPLE 6

4-N-glycyl-4,5'-dihydro-antibiotic AX-127B-1

To a stirred solution of 2.0 g of 4,5'-dihydro-antibiotic AX-127B-1, 30 ml of water and 60 ml of methanol, cooled in an ice bath at 0° C., are added 4.44 g of N-(benzyloxycarbonyl)succinimide. Stirring is continued at 0° C. for 3 hours, and then at ambient temperature for 22 hours. The major portion of the methanol is evaporated under reduced pressure and the residue is shaken with a mixture of chloroform and water. The chloroform solution is washed with water and dried over magnesium sulfate. The chloroform is evaporated and the residue is chromatographed on silica gel packed and eluted with a solvent system composed of chloroform-methanol-concentrated ammonium hydroxide[23.4:1:4:0.1(v/v/v/v)] to provide 1,6',3'',6'' tetra-N-benzyloxycarbonyl-4',5'-dihydro-antibiotic AX-127B-1. To a stirred solution of the latter, (2.3 g), 0.85 g of N-benzyloxycarbonylglycine, and 1.0 g of 1-hydroxybenzotriazole monohydrate in 12.0 ml of tetrahydrofuran, are added 1.0 g of N,N'-dicyclohexylcarbodiimide dissolved in 6.0 ml of tetrahydrofuran. And additional 6.0 ml of tetrahydrofuran is used to rinse all the dicyclohexylcarbodiimide into the reaction vessel. Stirring is continued at room temperature for 24 hours, and insoluble N,N'-dicyclohexylurea is removed by filtration with a sintered glass funnel. Removal of the tetrahydrofuran under reduced pressure gives a yellow residue which is chromatographed on a column of silica gel, packed and eluted with a solvent system consisting of benzenemethanol-95% ethanol-concentrated ammonium hydroxide[23.5:1.4:2.0:0.2(v/v/v/v)]. Fractions rich in penta-N-benzyloxycarbonyl-4-n-glycyl -4',5'-dihydro-antiobiotic AX-127B-1 are collected and rechromatographed on a column of Sephadex LH-20 gel prepared and eluted with 95% ethanol. Appropriate fractions are combined to give the tetra-N-protected intermediate. Hydrogenolysis in 150 ml of 0.2 N hydrochloric acid in methanol for 4 hours under 3 atmospheres of hydrogen in the presence of 0.8 g of 5% palladium on carbon and removal of the catalyst by filtration followed was evaporation of the methanol under reduced pressure, removal of residual water and excess acid by codistillation with methanol under reduced pressure provides the desired product, 4-N-glycyl-4',5'-dihydro-antibiotic AX-127B-1 as the pentahydrochloride salt.

EXAMPLE 7

By substituting N-benzyloxycarbonylsarcosine for N-benzyloxycarbonylglycine in the procedure of Example 6, 4-N-sarcosyl-4',5'-dihydro-antibiotic AX-127B-1 is obtained.

EXAMPLE 8

By substituting N-benzyloxycarbonyl-β-alanine for N-benzyloxycarbonylglycine in the procedure of Example 6, 4-N-β-alanyl-4′,5′-dihydro-antibiotic AX-127B-1 is obtained.

EXAMPLE 9

4-N-L-leucylglycyl-4′,5′-dihydro-antibiotic AX-127B-1 is obtained by substituting N-benzyloxycarbonylleucylglycine for N-benzyloxycarbonylglycine in the procedure of Example 6.

EXAMPLE 10

4-N-(DL-2-hydroxy-4-aminobutyryl)-4′,5′-dihydro-antibiotic AX-127B-1 is prepared by substituting N-benzyloxycarbonyl-DL-2-hydroxy-4-aminobutyric acid for N-benzyloxycarbonylglycine in the procedure of Example 6.

EXAMPLE 11

4-N-(N,N-Dimethylglycyl)-4′,5′-dihydro-antibiotic AX-127B-1 is prepared by substituting N-benzyloxycarbonyl-N,N-dimethylglycine for N-benzyloxycarbonylglycine in the procedure of Example 6.

EXAMPLE 12

4-N-Histidyl-4′,5′-dihydro-antibiotic AX-127B-1 is prepared by substituting N-benzyloxycarbonylhistidine for N-benzyloxycarbonylglycine in the procedure of Example 6.

EXAMPLE 13

4-N-Phenylalanyl-4′,5′-dihydro-antibiotic AX-127B-1 is prepared by substituting N-benzyloxycarbonylphenylalanine for N-benzyloxycarbonylglycine in the procedure of Example 6.

EXAMPLE 14

4-N-Leucyl-4′5′-dihydro-antibiotic AX-127B-1 is prepared by substituting N-benzyloxycarbonylleucine for N-benzyloxycarbonylglycine in the procedure of Example 6.

EXAMPLE 15

4-N-Acetyl-4′,5′-dihydro-antibiotic AX-127B-1 is prepared by substituting N-benzyloxycarbonylacetic acid for N-benzyloxycarbonyl-glycine in the procedure of Example 6.

EXAMPLE 16

4-N-Propionyl-4′,5′-dihydro-antibiotic AX-127B-1 is prepared by substituting N-benzyloxy-carbonylpropionic acid for N-benzyloxy-carbonylglycine in the procedure of Example 6.

EXAMPLE 17

4-N-Butyryl-4′,5′-dihydro-antibiotic AX-127B-1 is prepared by substituting N-benzyloxycarbonylbutyric acid for N-benzyloxycarbonylglycine in the procedure of Example 6.

EXAMPLE 18

4-N-(DL-2-Hydroxy-3-aminopropionyl)glycyl-4′,5′-dihydro-antibiotic AX-127B-1 is prepared by substituting N-benzyloxycarbonyl-DL-2-hydroxy-3-aminopropionylglycine for N-benzyloxycarbonylglycine in the procedure of Example 6.

EXAMPLE 19

4-N-(DL-2-Hydroxy-3-aminopropionyl)-4′,5′-dihydro-antibiotic AX-127B-1 is prepared by substituting N-benzyloxycarbonyl-DL-2-hydroxy-3-aminopropionic acid for N-benzyloxycarbonylglycine in the procedure of Example 6.

EXAMPLE 20–40

Following the procedure of Example 6 and by substituting the appropriate N-protected intermediate for N-benzyloxycarbonylglycine, the following compounds are obtained:

4-N-Glycyl-2′-N-des-β-lysyl-4′,5′-dihydro-antibiotic AX-127B-1;
4-N-Sarcosyl-2′-N-des-β-lysyl-4′,5′-dihydro-antibiotic AX-127B-1;
4-N-β-Alanyl-2′-N-des-β-lysyl-4′,5′-dihydro-antibiotic AX-127B-1;
4-N-Leucyl-2′-N-des-β-lysyl-4′,5′-dihydro-antibiotic AX-127B-1;
4-N-Histidyl-2′-N-des-β-lysyl-4′,5′-dihydro-antibiotic AX-127B-1;
4-N-Phenylalanyl-2′-N-des-β-lysyl-4′,5′-dihydro-antibiotic AX-127B-1;
4-N-Leucylglycyl-2′-N-des-β-lysyl-4′,5′-dihydro-antibiotic AX-127B-1;
4-N-(N,N-dimethylglycyl)-2′-N-des-β-lysyl-4′,5′-dihydro-antibiotic-AX-127B-1;
4-N-Valyl-2′-N-des-β-lysyl-4′,5′-dihydro-antibiotic-AX-127B-1;
4-N-Threonyl-2′-N-des-β-lysyl-4′,5′-dihydro-antibiotic-AX-127B-1;
4-N-Prolyl-2′-N-des-β-lysyl-4′,5′-dihydro-antibiotic-AX-127B-1;
4-N-Tyrosyl-2′-N-des-β-lysyl-4′,5′-dihydro-antibiotic-AX-127B-1;
4-N-Glutamyl-2′-N-des-β-lysyl-4′,5′-dihydro-antibiotic-AX-127B-1;
4-N-Glutaminyl-2′-N-des-β-lysyl-4′,5′-dihydro-antibiotic-AX-127B-1;
4-N-Methionyl-2′-N-des-β-lysyl-4′,5′-dihydro-antibiotic-AX-127B-1;
4-N-Formyl-2′-N-des-β-lysyl-4′,5′-dihydro-antibiotic AX-127B-1;
4-N-Acetyl-2′-N-des-β-lysyl-4′,5′-dihydro-antibiotic AX-127B-1;
4-N-Propionyl-2′-N-des-β-lysyl-4′,5′-dihydro-antibiotic AX-127B-1;
4-N-Butyryl-2′-N-des-β-lysyl-4′,5′-dihydro-antibiotic AX-127B-1;
4-N-Valeryl-2′-N-des-β-lysyl-4′,5′-dihydro-antibiotic AX-127B-1;
4-N-β-L-lysyl-2′-N-des-β-lysyl-4,5′-dihydro-antibiotic AX-127B-1;
4-N-(2-hydroxy-4-aminobutyryl)-2′-N-des-β-lysyl-4′,5′-dihydro-antibiotic AX-127B-1;
4-N-(2-hydroxy-3-aminopropionyl)-2′-N-des-β-lysyl-4′,5′-dihydro-antibiotic AX-127B-1′ etc.

EXAMPLE 41–58

Treatment of the 4-N-derivatives of Example 6–38 with diborane following the method of U.S. Pat. No. 4,187,296, provides the corresponding 4-N-alkyl derivatives of 4′,5′-dihydro-antibiotic AX-127B-1 and 2′-des-β-lysyl-4′,5′-dihydroantibiotic AX-127B-1.

Representative 4-N-alkyl derivatives include, but are not limited to:

4-N-Methyl-4′,5′-dihydro-antibiotic AX-127B-1;
4-N-Ethyl-4′,5′-dihydro-antibiotic AX-127B-1;
4-N-n-Propyl-4′,5′-dihydro-antibiotic AX-127B-1;
4-N-iso-Propyl-4′,5′-dihydro-antibiotic AX-127B-1;

4-N-n-Butyl-4′,5′-dihydro-antibiotic AX-127B-1;
4-N-sec-Butyl-4′,5′-dihydro-antibiotic AX-127B-1;
4-N-tert-Butyl-4′,5′-dihydro-antibiotic AX-127B-1;
4-N-n-Pentyl-4′,5′-dihydro-antibiotic AX-127B-1;
4-N-2,3-Dimethylpropyl-4′,5′-dihydro-antibiotic AX-127B-1;
4-N-n-Hexyl-4′,5′-dihydro-antibiotic AX-127B-1;
4-N-2-Hydroxyethyl-4′,5′-dihydro-antibiotic AX-127B-1;
4-N-2-Aminoethyl-4′,5′-dihydro-antibiotic AX-127B-1;
4-N-2-Aminohydroxyethyl-4′,5′-dihydro-antibiotic AX-127B-1;
4-N-2-Hydroxy-4-aminobutyl-4′,5′-dihydro-antibiotic AX-127B-1;
4-N-2-Hydroxy-3-aminopropyl-4′,5′-dihydro-antiobiotic AX-127B-1;
4-N-(N,N-Dimethylaminoethyl)-4′,5′-dihydro-antibiotic AX-127B-1;
4-N-Methyl-2′-des-β-lysyl-4′,5′-dihydro-antibiotic AX-127B-1;
4-N-2-Aminoethyl-2′-des-β-lysyl-4′,5′-dihydro-antibiotic AX-127B-1; etc.

The present invention includes within its scope pharmaceutical compositions comprising, as an active ingredient, an antibiotic AX-127B-1 derivative of this invention, or a pharmaceutically acceptable salt thereof, in association with a pharmaceutically acceptable carrier or diluent. The compounds are administered parenterally (i.e. by intramuscular, intravenous, intraperitoneal or subcutaneous routes of injection) or, to sterilize the gastrointestinal tract, by oral routes of administration, and can be formulated in dosage forms appropriate for each route of administration.

Solid dosage forms for oral administration include capsules, tablets, pills, powders and granules. In such solid dosage forms, the active compound is admixed with at least one inert carrier or diluent such as sucrose, lactose or starch. Such dosage forms can also comprise buffering agents. Tablets and pills can additionally be prepared with enteric coatings.

Liquid dosage forms for oral administration include pharmaceutically acceptable emulsions, solutions, suspensions, syrups and elixirs containing inert diluents. Besides such inert diluents, the compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectible medium immediately after use.

The dosage of the active ingredient in the composition may be varied to accomodate pediatric dosages, adult dosages, etc. However, it is necessary that the amount of active ingredient shall be such that a suitable dosage form is obtained.

The following examples further illustrate the present invention.

EXAMPLE 59

Tablets weighing 250 mg and having the following composition are formulated:

| Ingredient | Mg |
|---|---|
| 4′,5′-Dihydro-antibiotic AX-127B-1 | 100 |
| Starch | 120 |
| Colloidal silica | 27 |
| Magnesium stearate | 3 |

EXAMPLE 60

Sterile 10 ml ampules are prepared containing 10 mg/kg of 2′-N-des-β-lysyl-4,5′-dihydro-antibiotic AX-127B-1 tri-hydrochloride, 0.1 percent sodium bisulfate, 0.7 percent sodium chloride, 0.5 percent chlorobutanol and water q.s.

I claim:

1. An antibiotic AX-127B-1 derivative represented by the formula

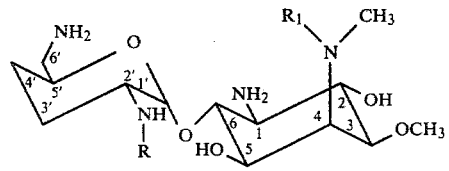

wherein: R is selected from the group consisting of hydrogen or β-lysyl; $R_1$ is selected from the group consisting of hydrogen, acyl, aminoacyl, diaminoacyl, N-loweralkylaminoacyl, N,N-diloweralkylaminoacyl, hydroxy-substituted aminoacyl, loweralkyl, aminoloweralkyl, diaminoloweralkyl, hydroxyloweralkyl, N-loweralkylaminoloweralkyl, N,N-diloweralkylaminoloweralkyl, N-loweralkylaminohydroxyloweralkyl, and N,N-diloweralkylaminohydroxyloweralkyl; and the pharmaceutically acceptable salts thereof.

2. A compound of claim 1 wherein R is β-lysyl or a pharmaceutically acceptable salt thereof.

3. A compound of claim 2 wherein $R_1$ is hydrogen: 4′,5′-dihydro-antibiotic AX-127B-1 or a pharmaceutically acceptable salt thereof.

4. A compound of claim 2 wherein $R_1$ is selected from the group consisting of acyl, aminoacyl, diaminoacyl, N-loweralkylaminoacyl, N,N-diloweralkylaminoacyl and hydroxy-substituted aminoacyl or a pharmaceutically acceptable salt thereof.

5. A compound of claim 4: 4-N-glycyl-4′,5′-dihydro-antibiotic AX-127B-1 or a pharmaceutically acceptable salt thereof.

6. A compound of claim 4: 4-N-sarcosyl-4′,5′-dihydro-antibiotic AX-127B-1 or a pharmaceutically acceptable salt thereof.

7. A compound of claim 4: 4-N-β-alanyl-4′,5′-dihydro-antibiotic AX-127B-1 or a pharmaceutically acceptable salt thereof.

8. A compound of claim 4: 4-N-histidyl-4′,5′-dihydro-antibiotic AX-127B-1 or a pharmaceutically acceptable salt thereof.

9. A compound of claim 4: 4-N-leucyl-4′,5′-dihydro-antibiotic AX-127B-1 or a pharmaceutically acceptable salt thereof.

10. A compound of claim 4: 4-N-leucylglycyl-4',5'-dihydro-antibiotic AX-127B-1 or a pharmaceutically acceptable salt thereof.

11. A compound of claim 4: 4-N-(N,N-dimethylglycyl)-4',5'-dihydro-antibiotic AX-127B-1 or a pharmaceutically acceptable salt thereof.

12. A compound of claim 4: 4-N-threonyl-4',5'-dihydro-antibiotic AX-127B-1 or a pharmaceutically acceptable salt thereof.

13. A compound of claim 4: 4-N-methionyl-4',5'-dihydro-antibiotic AX-127B-1 or a pharmaceutically acceptable salt thereof.

14. A compound of claim 4: 4-N-prolyl-4',5'-dihydro-antibiotic AX-127B-1 or a pharmaceutically acceptable salt thereof.

15. A compound of claim 4: 4-N-glutamyl-4',5'-dihydro-antibiotic AX-127B-1 or a pharmaceutically acceptable salt thereof.

16. A compound of claim 4: 4-N-valyl-4',5'-dihydro-antibiotic AX-127B-1 or a pharmaceutically acceptable salt thereof.

17. A compound of claim 4: 4-N-glutaminyl-4',5'-dihydro-antibiotic AX-127B-1 or a pharmaceutically acceptable salt thereof.

18. A compound of claim 4: 4-N-acetyl-4',5'-dihydro-antibiotic AX-127B-1 or a pharmaceutically acceptable salt thereof.

19. A compound of claim 4: 4-N-propionyl-4',5'-dihydro-antibiotic AX-127B-1 or a pharmaceutically acceptable salt thereof.

20. A compound of claim 4: 4-N-butyryl-4',5'-dihydro-antibiotic AX-127B-1 or a pharmaceutically acceptable salt thereof.

21. A compound of claim 4: 4-N-valeryl-4',5'-dihydro-antibiotic AX-127B-1 or a pharmaceutically acceptable salt thereof.

22. A compound of claim 4: 4-N-(2-hydroxy-4-aminobutyryl)-4',5'-dihydro-antibiotic AX-127B-1 or a pharmaceutically acceptable salt thereof.

23. A compound of claim 4: 4-N-(2-hydroxy-3-aminopropionyl)-4',5'-dihydro-antibiotic AX-127B-1 or a pharmaceutically acceptable salt thereof.

24. A compound of claim 2 wherein $R_1$ is selected from the group consisting of: loweralkyl, aminoloweralkyl, N-loweralkylaminoloweralkyl, N,N-diloweralkylaminoloweralkyl, N-loweralkylaminohydroxyloweralkyl and N,N-diloweralkylaminohydroxyloweralkyl; or a pharmaceutically acceptable salt thereof.

25. A compound of claim 2: 4-N-methyl-4',5'-dihydro-antibiotic AX-127B-1 or a pharmaceutically acceptable salt thereof.

26. A compound of claim 2: 4-N-ethyl-4',5'-dihydro-antibiotic AX-127B-1 or a pharmaceutically acceptable salt thereof.

27. A compound of claim 2: 4-N-n-propyl-4',5'-dihydro-antibiotic AX-127B-1 or a pharmaceutically acceptable salt thereof.

28. A compound of claim 2: 4-N-iso-propyl-4',5'-dihydro-antibiotic AX-127B-1 or a pharmaceutically acceptable salt thereof.

29. A compound of claim 2: 4-N-n-butyl-4',5'-dihydro-antibiotic AX-127B-1 or a pharmaceutically acceptable salt thereof.

30. A compound of claim 2: 4-N-iso-butyl-4',5'-dihydro-antibiotic AX-127B-1 or a pharmaceutically acceptable salt thereof.

31. A compound of claim 2: 4-N-tert-butyl-4',5'-dihydro-antibiotic AX-127B-1 or a pharmaceutically acceptable salt thereof.

32. A compound of claim 1 wherein R is hydrogen or a pharmaceutically acceptable salt thereof.

33. A compound of claim 32 wherein $R_1$ is hydrogen: 2'-des-N-β-lysyl-4',5'-dihydro-antibiotic AX-127B-1 or a pharmaceutically acceptable salt thereof.

34. A compound of claim 32 wherein $R_1$ is selected from the group consisting of acyl, aminoacyl, diaminoacyl, N-loweralkylaminoacyl, N,N-deloweralkylaminoacyl and hydroxy-substituted aminoacyl or a pharmaceutically acceptable salt thereof.

35. A compound of claim 34: 4-N-glycyl-2'-des-N-β-lysyl-4',5'-dihydro-antibiotic AX-127B-1 or a pharmaceutically acceptable salt thereof.

36. A compound of claim 34: 4-N-sarcosyl-2'-des-N-β-lysyl-4',5'-dihydro-antibiotic AX-127B-1 or a pharmaceutically acceptable salt thereof.

37. A compound of claim 34: 4-N-β-alanyl-2'-des-N-β-lysyl-4',5'-dihydro-antibiotic AX-127B-1 or a pharmaceutically acceptable salt thereof.

38. A compound of claim 34: 4-N-istidyl-2'-des-N-β-lysyl-4',5'-dihydro-antibiotic AX-127B-1 or a pharmaceutically acceptable salt thereof.

39. A compound of claim 34: 4-N-leucyl-2'-N-des-β-lysyl-4',5'-dihydro-antibiotic AX-127B-1 or a pharmaceutically acceptable salt thereof.

40. A compound of claim 34: 4-N-leucylglycyl-2'-N-des-β-lysyl-4',5'-dihydro-antibiotic AX-127B-1 or a pharmaceutically acceptable salt thereof.

41. A compound of claim 34: 4-N-(N,N-dimethylglycyl)-2'-N-des-β-lysyl-4',5'-dihydro-antibiotic AX-127B-1 or a pharmaceutically acceptable salt thereof.

42. A compound of claim 34: 4-N-threonyl-2'-N-des-β-lysyl-4',5'-dihydro-antibiotic AX-127B-1 or a pharmaceutically acceptable salt thereof.

43. A compound of claim 34: 4-N-methionyl-2'-N-des-β-lysyl-4',5'-dihydro-antibiotic AX-127B-1 or a pharmaceutically acceptable salt thereof.

44. A compound of claim 34: 4-N-prolyl-2'-N-des-β-lysyl-4',5'-dihydro-antibiotic AX-127B-1 or a pharmaceutically acceptable salt thereof.

45. A compound of claim 34: 4-N-glutamyl-2'-N-des-β-lysyl-4',5'-dihydro-antibiotic AX-127B-1 or a pharmaceutically acceptable salt thereof.

46. A compound of claim 34: 4-N-valyl-2'-des-β-lysyl-4',5'-dihydro-antibiotic AX-127B-1 or a pharmaceutically acceptable salt thereof.

47. A compound of claim 34: 4-N-glutaminyl-2'-N-des-β-lysyl-4',5'-dihydro-antibiotic AX-127B-1 or a pharmaceutically acceptable salt thereof.

48. A compound of claim 34: 4-N-acetyl-2'-N-des-β-lysyl-4',5'-dihydro-antibiotic AX-127B-1 or a pharmaceutically acceptable salt thereof.

49. A compound of claim 34: 4-N-propionyl-2'-N-des-β-lysyl-4',5'-dihydro-antibiotic AX-127B-1 or a pharmaceutically acceptable salt thereof.

50. A compound of claim 34: 4-N-butyryl-2'-N-des-β-lysyl-4',5'-dihydro-antibiotic AX-127B-1 or a pharmaceutically acceptable salt thereof.

51. A compound of claim 34: 4-N-valeryl-2'-N-des-β-lysyl-4',5'-dihydro-antibiotic AX-127B-1 or a pharmaceutically acceptable salt thereof.

52. A compound of claim 34: 4-N-(2-hydroxy-4-aminobutyryl)-2'-N-des-β-lysyl-4',5'-dihydro-antibiotic AX-127B-1 or a pharmaceutically acceptable salt thereof.

53. A compound of claim 34: 4-N-(2-hydroxy-3-aminopropionyl)-2'-N-des-β-lysyl-4',5'-dihydro-antibiotic AX-127B-1 or a pharmaceutically acceptable salt thereof.

54. A compound of claim 32 where $R_1$ is selected from the group consisting of: loweralkyl, aminoloweralkyl, N-loweralkylaminoloweralkyl, N,N-diloweralkylaminoloweralkyl, N-loweralkylaminohydroxyloweralkyl and N,N-diloweralkylaminohydroxyloweralkyl; or a pharmaceutically acceptable salt thereof.

55. A compound of claim 54: 4-N-methyl-4,5'-dihydro-antibiotic AX-127B-1 or a pharmaceutically acceptable salt thereof.

56. A compound of claim 54: 4-N-ethyl-4,5'-dihydro-antibiotic AX-127B-1 or a pharmaceutically acceptable salt thereof.

57. A compound of claim 54: 4-N-n-propyl-4,5'-dihydro-antibiotic AX-127B-1 or a pharmaceutically acceptable salt thereof.

58. A compound of claim 54: 4-N-iso-propyl-4',5'-dihydro-antibiotic AX-127B-1 or a pharmaceutically acceptable salt thereof.

59. A compound of claim 54: 4-N-n-butyl-4',5'-dihydro-antibiotic AX-127B-1 or a pharmaceutically acceptable salt thereof.

60. A compound of claim 54: 4-N-iso-butyl-4',5'-dihydro-antibiotic AX-127B-1 or a pharmaceutically acceptable salt thereof.

61. A compound of claim 54: 4-N-tert-butyl-4',5'-dihydro-antibiotic AX-127B-1 or a pharmaceutically acceptable salt thereof.

62. A compound of claim 54: 4-N-β-aminoethyl-4',5'-dihydro-antibiotic AX-127B-1 or a pharmaceutically acceptable salt thereof.

63. A compound of claim 54: 4-N-β-hydroxyethyl-4',5'-dihydro-antibiotic AX-127B-1 or a pharmaceutically acceptable salt thereof.

64. A compound of claim 54: 4-N-β-aminohydroxyethyl-4',5'-dihydro-antibiotic AX-127B-1 or a pharmaceutically acceptable salt thereof.

65. A pharmaceutical composition comprising an antibacterially effective amount of a compound of claim 1 and a pharmaceutically acceptable carrier or diluent.

66. A composition of claim 65 wherein said compound is 4',5'-dihydro-antibiotic AX-127B-1 or a pharmaceutically acceptable salt thereof.

67. A compositon of claim 65 wherein said compound is 2'-N-des-β-lysyl-4',5'-dihydro-antibiotic AX-127B-1 or a pharmaceutically acceptable salt thereof.

68. A method of treating mammalian patients suffering from infection by a susceptible organism comprising administering a therapeutically effective amount of a compound of claim 1 to said patient.

* * * * *

UNITED STATES PATENT AND TRADEMARK OFFICE
CERTIFICATE OF CORRECTION

PATENT NO. : 4,338,309
DATED : July 6, 1982
INVENTOR(S) : Paul Kurath

It is certified that error appears in the above—identified patent and that said Letters Patent is hereby corrected as shown below:

In column 12, line 47, after 2', please insert . . . -N . . .

Signed and Sealed this

First Day of March 1983

[SEAL]

Attest:

GERALD J. MOSSINGHOFF

*Attesting Officer*   *Commissioner of Patents and Trademarks*